US009348067B2

(12) United States Patent
Vogtmeier et al.

(10) Patent No.: US 9,348,067 B2
(45) Date of Patent: May 24, 2016

(54) TILTED GRATINGS AND METHOD FOR PRODUCTION OF TILTED GRATINGS

(75) Inventors: Gereon Vogtmeier, Aachen (DE); Klaus Juergen Engel, Aachen (DE); Thomas Koehler, Norderstedt (DE); Ewald Roessl, Ellerau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 693 days.

(21) Appl. No.: 13/319,196

(22) PCT Filed: Jun. 9, 2010

(86) PCT No.: PCT/IB2010/052555
§ 371 (c)(1),
(2), (4) Date: Nov. 7, 2011

(87) PCT Pub. No.: WO2010/146498
PCT Pub. Date: Dec. 23, 2010

(65) Prior Publication Data
US 2012/0057677 A1    Mar. 8, 2012

(30) Foreign Application Priority Data

Jun. 16, 2009 (EP) .................................... 09162787

(51) Int. Cl.
*G21K 1/00* (2006.01)
*G02B 5/18* (2006.01)
*A61B 6/00* (2006.01)

(52) U.S. Cl.
CPC .............. *G02B 5/1857* (2013.01); *A61B 6/484* (2013.01); *G21K 2201/06* (2013.01); *G21K 2207/005* (2013.01)

(58) Field of Classification Search
CPC .............................. A61B 6/484; G01N 23/207
USPC ........................................................... 378/62
See application file for complete search history.

(56) References Cited

U.S. PATENT DOCUMENTS

| 5,009,484 A | | 4/1991 | Gerritsen | |
| 5,116,461 A | * | 5/1992 | Lebby | G02B 5/1857 |
| | | | | 204/192.34 |
| 5,812,629 A | * | 9/1998 | Clauser | 378/62 |

(Continued)

FOREIGN PATENT DOCUMENTS

| CN | 101013613 A | 8/2007 |
| EP | 1731099 A1 | 12/2006 |

(Continued)

OTHER PUBLICATIONS

Atsushi Momose, Wataru Yashiro, Yoshihiro Takeda, Yoshio Suzuki and Tadashi Hattori, "Phase Tomography by X-ray Talbot Interferometry for Biological Imaging", Japanese Journal of Applied Physics, Jpan Society of Applied Physics, vol. 45, No. 6A, 2006, pp. 5254-5262 JP.

(Continued)

*Primary Examiner* — Hoon Song

(57) ABSTRACT

The present invention relates to phase-contrast imaging which visualizes the phase information of coherent radiation passing a scanned object. Focused gratings are used which reduce the creation of trapezoid profile in a projection with a particular angle to the optical axis. A laser supported method is used in combination with a dedicating etching process for creating such focused grating structures.

22 Claims, 6 Drawing Sheets

(56) References Cited

U.S. PATENT DOCUMENTS

| | | |
|---|---|---|
| 2007/0057500 A1 | 3/2007 | Bunmann et al. |
| 2007/0183579 A1 | 8/2007 | Baumann et al. |
| 2007/0183582 A1* | 8/2007 | Baumann et al. .............. 378/145 |
| 2008/0003528 A1 | 1/2008 | Gaylord et al. |
| 2008/0317213 A1 | 12/2008 | Hempel et al. |
| 2009/0147923 A1* | 6/2009 | Kammel et al. .............. 378/154 |

FOREIGN PATENT DOCUMENTS

| | | |
|---|---|---|
| EP | 1879020 A1 | 1/2008 |
| JP | 2003329821 A | 11/2003 |
| JP | 2005004068 A | 1/2005 |
| JP | 2007206075 A | 8/2007 |
| WO | 2007057500 A1 | 5/2007 |
| WO | 2008029107 A2 | 3/2008 |
| WO | 2009069040 A1 | 6/2009 |

OTHER PUBLICATIONS

Franz Pfeiffer, Timm Weitkamp, Oliver Bunk, and Christian David, "Phase Retrieval and Differential Phase-Contrast Imaging with Low-Brilliance X-ray Sources", Nature Physics, Nature Publishing Group, London, GB, 1038/NPHYS265, Mar. 26, 2006, pp. 258-261, XP002422783, ISSN: 1745-2473.

Timm Weitkamp, Ana Diaz, Bernd Nohammer, Franz Pfeiffer, Torben Rohbeck, Peter Cloetens, Marco Stampanoni and Christian David, "Hard X-ray Phase Imaging and Tomography with a Grating Interferometer", Proceedings of the International Society for Optical Engineering, USA, vol. 5535, No. 1, Oct. 1, 2004, pp. 137-142, XP002397630, ISSN: 0277-786X.

* cited by examiner

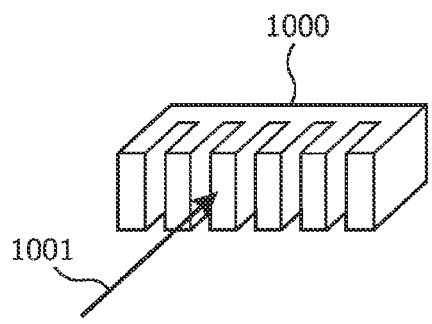
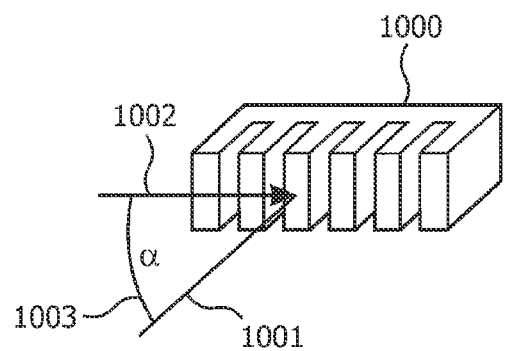
FIG. 10    FIG. 11
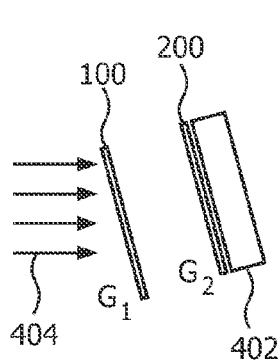
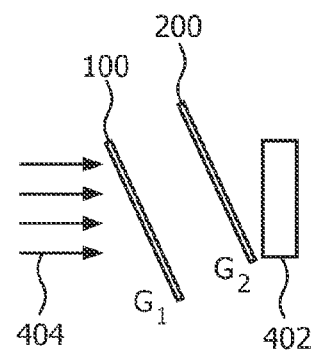
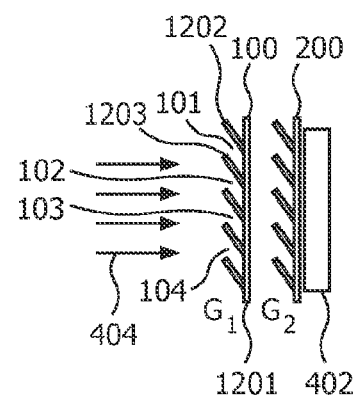
FIG. 12a    FIG. 12b    FIG. 12c
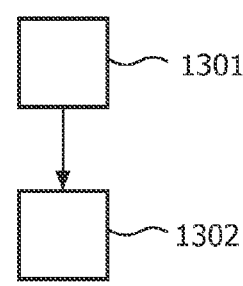
FIG. 13

TILTED GRATINGS AND METHOD FOR PRODUCTION OF TILTED GRATINGS

FIELD OF THE INVENTION

The invention relates to phase-contrast imaging. In particular, the invention relates to a grating for a phase-contrast imaging apparatus, a phase-contrast imaging apparatus comprising such a grating, and a method of fabricating a grating for a phase-contrast imaging apparatus.

BACKGROUND OF THE INVENTION

For examination of objects of interest with electromagnetic radiation, visible or invisible light or X-rays may be used. X-ray differential phase-contrast imaging (DPCI) visualizes the phase information of coherent X-rays passing a scanned object. In addition to classical X-ray transmission imaging, DPCI determines not only the absorption properties of a scanned object along a projection line, but also the phase shift of the transmitted X-rays, and thus provides variable additional information usable for contrast enhancement, material composition or dose reduction.

Recently, a group at Paul-Scherrer Institute, Villingen, Switzerland has introduced a realization of DPCI (see for example EP 1 731 099 A1, EP 1 879 020 A1, Pfeiffer et al., Nature Physics 2, 258 (2006).

While older differential or non-differential PCI methods may suffer from the requirement of highly monochromatic and coherent X-ray sources, the above method may allow the use of standard X-ray sources, i.e. X-ray tubes, with an additional source grating which may assure coherence through small openings. After the object of interest to be imaged, a phase-shifting grating (G1) is placed (working as a "beam splitter"). The resulting interference pattern (see FIG. 2) contains the required information about the beam phase shift in the relative position of its minima and maximal (typically in the order of several micrometers). Since a common X-ray detector (typical resolution in the order of 150 μm) is not able to resolve such fine structures, the interference is sampled with a phase-analyzer grating (also known as "absorber grating G2") which features a periodic pattern of transmitting and absorbing strips with the periodicity similar to that of the interference pattern.

The similar periodicity produces a Moire pattern behind the grating with a much larger periodicity, which is detectable by a common X-ray detector (see FIG. 3). To obtain the differential phase shift, the analyzer grating (absorber grating) G2 needs to be shifted laterally by fractions of the grating pitch p (typically of the order of 1 μm), referred to as "phase stepping". The phase shift can be extracted from the particular Moire pattern measured for each position of the analyzer grating. In an extension, computed tomography of phase-shift with hard X-rays may also be performed.

However, in particular in the case of cone-beam geometry, strong phase-contrast distortions may arise in regions outside the centre of the field of view (FOV).

SUMMARY OF THE INVENTION

It may be desirable to have an imaging system producing images with less phase-contrast distortions.

The invention relates to a grating for phase-contrast imaging apparatus for examining an object of interest, a phase-contrast imaging apparatus having such a grating and a method of fabricating such a grating. Further features of exemplary embodiments of the invention are stated in the dependent claims.

It should be noted that the features which are in the following described for example with respect to the phase grating may also be part of the imaging apparatus, and vice versa. Furthermore, all features which are in the following described with respect to the grating/gratings correlate to respective method steps for fabricating the grating/the gratings.

According to an exemplary embodiment of the invention, a grating for a phase-contrast imaging apparatus for examining an object of interest is provided, the grating having a primary axis which is arranged in a direction towards a source of radiation when the grating is installed in the imaging apparatus. The grating comprises a wafer material and a first trench inside the wafer material having a depth in a first direction, wherein the first direction is different from the primary axis, such that the first trench is tilted with respect to the primary axis.

In other words, the trench is not drilled or etched or "fabricated" by simply "digging" into a substrate in the direction of the primary axis, but at a tilted angle with respect to the primary axis. The primary axis is typically perpendicular to a surface of the substrate.

It should be noted that the "trench" has not necessarily to be drilled or etched into a substrate, but it can also be "grown" on the substrate by growing the walls of the trench onto the substrate. One possibility may be a prefabrication step in which a sacrificial layer of material is provided on the substrate into which gaps for the later walls are cut out (for example by electronic beam lithography followed by an appropriate etching step). Then, in the next step, the walls of the trenches can be grown onto the substrate, for example by sputtering. In a third step, the remaining sacrificial layer can be removed, if necessary.

It should further be noted that grating is defined as structure with trenches and trenches could be filled with air for the phase grating or with absorbing material for absorption grating.

In case the grating is a segmented or two-dimensional structure the primary axis is the primary axis for an individual a segment.

Thus growing of layers is an alternative to etching although it may take more time for the production compared to etching in silicon. Methods like 3D printing or laser sintering of plastic/metal are also possible even with a feature size of less than 50 μm. A fine powder grain size may allow sintering of such smaller structures.

According to another exemplary embodiment of the invention, the grating comprises a second trench inside the wafer material. The first trench is tilted by a first angle with respect to the primary axis and the second trenches tilted by a second angle with respect to the primary axis. The first angle is smaller than the second angle.

According to another exemplary embodiment of the invention, a sequence of trenches is provided, wherein each trench of the sequence of trenches is tilted by a respective angle with respect to the (possibly segmented) primary axis, wherein the respective angle increases from trench to trench.

In other words, when moving from trench to trench, each following trench is tilted a bit more than the trench before. For example, the first trench is tilted by an angle of −20° with respect to the primary axis (which points towards the source of electromagnetic radiation when the grating is inserted into imaging apparatus), the following trench is only tilted by −19.9999°, the following trench by −19.9998°, and so on. The middle trench is not tilted and the trench following the middle trench is tilted by 0.0001° and so on wherein the last trench is tilted by +20°.

If one looks to one grating with a distance from trench to trench of 1 μm, a distance of about 1 m from source to grating/detector and a detector size of about 30 cm then the angular tilt from trench to trench is much smaller—more in the range of 0.0001° to 0.001° per trench—so very precise alignment and modification from structure to structure.

This may allow for an operation of the imaging apparatus in a focused geometry.

According to another exemplary embodiment of the invention, the trenches are linear trenches, which are for example arranged parallel to each other in a plane perpendicular to the primary axis.

In other words, when looking along the primary axis of the grating, each trench extends linearly along the plane perpendicular to the primary axis and is arranged parallel to the other trenches (although most trenches are tilted with respect to the direction of the primary axis).

According to another exemplary embodiment of the invention, the primary axis of the grating is perpendicular to a surface of the grating.

According to another exemplary embodiment of the invention, a phase-contrast imaging apparatus for examining an object of interest is provided. The apparatus comprises a source for emitting a beam of radiation, a detector for detecting radiation and a phase grating positioned between the source and the detector. The detector is adapted for detecting the radiation after it has passed the object of interest and the phase grating (G1). Furthermore, the phase grating has a focused geometry.

According to another exemplary embodiment of the invention, the imaging apparatus has a cone-beam geometry like e.g. C-arm systems or CT systems.

According to another exemplary embodiment of the invention, the imaging apparatus is adapted in form of a Talbot interferometry imaging apparatus.

According to another exemplary embodiment of the invention, the imaging apparatus has an optical axis pointing from the source to the detector, wherein the grating has a primary axis which is arranged in the direction of the optical axis when the grating is installed in the imaging apparatus. The phase grating of the phase-contrast imaging apparatus is one of the gratings which have been described above and will be described in the following in more detail.

According to another exemplary embodiment of the invention, the imaging apparatus comprises a second grating which is an absorption grating (G2) positioned in front of the detector and after the first grating G1. The second grating has also a focused geometry. In particular, the second grating G2 may have the same features as the above and in the following described gratings.

According to another exemplary embodiment of the invention, the imaging apparatus further comprises a third grating which is an absorption grating (G0) having a trapezoid geometry and position between the source and the phase grating and which allows for a at least partially coherent illumination of the phase grating.

It should be noted that the described gratings can be one-dimensional gratings or also two-dimensional gratings.

According to another exemplary embodiment of the invention, the imaging apparatus further comprises an actuator, such as a piezo actuator or a stepper motor, wherein the beam of radiation emitted by the source has an optical axis and wherein the stepper motor is adapted for moving at least one of the gratings G0, G1 or G2 perpendicular to the optical axis of the beam of radiation emitted by the source and/or for changing an effective trench depth for the incident beam of radiation by tilting the grating to a certain angle, e.g. for adaptation of the transmission length in grating to energy dependent phase shift.

The imaging apparatus may comprise a motor or actuator adapted for rotating the phase grating G1 and/or the absorption grating G2. Also, two motors or actuators can be provided, each for one grating or even two for each grating to control the angular tile in two directions.

Thus, it is possible to control the angle α (which is the angle between the grating normal and the rays emitted from the source), even during a measurement.

According to another exemplary embodiment of the invention, the source is an X-ray source, wherein the apparatus is adapted as an X-ray phase differential phase-contrast imaging apparatus.

According to another exemplary embodiment of the invention, the imaging apparatus is adapted as an optical imaging apparatus, wherein the source is a light source. The radiation used for probing the object of interest is, in this case, an optical radiation beam with a wavelength within the range of for example 400 nm to 1.400 nm.

According to another exemplary embodiment of the invention, a method of fabricating an above and in the following described grating for a phase-contrast imaging apparatus for examining an object of interest is provided. The method comprises the steps of writing, with a laser beam, a first trench or trench structure into a wafer material and optimizing of the geometry/finishing by smoothing surfaces of the written first trench by etching, wherein the first trench has a depth in a first direction and wherein the first direction is different from the primary axis, such that the first trench is tilted by a first angle with respect to the primary axis.

Furthermore, the method may comprise the additional steps of writing additional trenches which are all tilted with respect to the primary axis. Each trench may be tilted a bit more, when moving from trench to trench. Thus, for example 2D-structures or circular can be provided.

Furthermore, the method may comprise the additional step of filling at least a first trench (for example all trenches) with an absorbing material. As already noted, the performance of X-ray differential phase-contrast imaging with a Talbot interferometer may be affected by a strong phase-contrast deterioration in regions outside the centre FOV when using rectangularly structured gratings. Such strong phase-contrast deterioration may always occur in case of non-focused gratings G0, G1 and G2, as a rectangular structure creates a trapezoid profile in a projection with a particular angle to the optical axis.

It may be seen as a gist of the invention that a laser supported method in combination with a dedicated etching process for creating such focused grating structures is provided. As the etching process is an isotropic process it is necessary to bring trenches in the preferred direction into the silicon. It is possible to drill holes in silicon and also to structure areas with a laser or other electromagnetic radiation beam methods. However, the surface structure of a laser drilled hole may be not as perfect as it is needed for the gratings. The proposed method is a combination of at least two steps:

1. Trenches are "written" into the silicon wafer along the grating line direction but with a slightly increased angle from trench to trench. This gives the rough "focusing" direction of the overall structure. During the trench "writing" process the laser has to be focused to the different depth inside the silicon and also the beam shape has to be adapted to achieve an almost great profile line at the side of the trench.

The beam shape is adapted by performing an adaptive position dependent focussing of the optical lens system of a laser to get a defined beam profile (focussing to certain depth inside the material with defined beam width).

2. The post-processing step is an etching step to "clean" and "smoothen" the surfaces and to optimize the grating structure.

For example wet or DRIE etching (like known Bosch process) may be used depending on geometry, silicon wafer (crystal structure) alignment to trench structures and also depending on trench profile and geometry.

This combination of anisotropic and isotropic processing steps allows a defined structuring of the wafer material to build focussed structures for the intended phase contrast imaging system.

It should also be noted, that the gratings G0, G1, G2 can be fabricated with the help of electron beam lithography instead of laser beam writing of the trench structures into the wafer material.

For example, the electron beam can be used for removing or exposing certain regions of the substrate or of a photoresist layer thereon. In order to "write" trenches with desired, varying tilt angles α, the substrate can be mounted on a positioning device which is adapted not only for linearly positioning the substrate in three dimensions but also for rotating the substrate such that different angles between the incident electron beam and the substrate surface can be provided. For providing such a positioning of the substrate with high accuracy, rotators and linear positioners based on so-called "slip-stick" technology can be used. Such nano-positioners are for example available from the company attotube systems AG.

After electron beam lithography, and after removal of the exposed photoresist, a sputtering step can be performed in order to grow the tilted trenches on the substrate.

After a lift-off step, the surfaces of the grown trench structure can be smoothened, for example by a corresponding etching step.

It is another gist of the invention that such gratings with "tilted" trenches are used for phase-contrast imaging, for example for X-ray differential phase-contrast imaging. To further improve image quality, the first absorption grating G0 may have a trapezoid geometry (symmetric or even asymmetric).

One advantage of tilting the gratings of the imaging system in a controlled way inside the beam is that higher effective design energies with the same physical aspects ratio of the trench may be obtained and the system could be tuned to dedicated energy parameters without modifying the grating geometry.

These and other aspects of the invention will become apparent from and elucidated with reference to the embodiments described hereinafter.

Exemplary embodiments of the invention will be described in the following, with reference to the following drawings.

BRIEF DESCRIPTION OF THE DRAWINGS

FIG. 10 shows a perspective view of a grating with radiation impinging in normal direction.

FIG. 11 shows the grating of FIG. 10 with radiation impinging under an angle α with respect to the normal direction.

FIG. 12A shows a different setup for an imaging apparatus according to an exemplary embodiment of the invention.

FIG. 12B shows a setup for an imaging apparatus according to another exemplary embodiment of the present invention.

FIG. 12C shows a setup with an imaging apparatus with phase grating and absorption grating according to another exemplary embodiment of the invention.

FIG. 13 shows a flow-chart of a method according to an exemplary embodiment of the invention.

DETAILED DESCRIPTION OF EMBODIMENTS

Figure 1A:
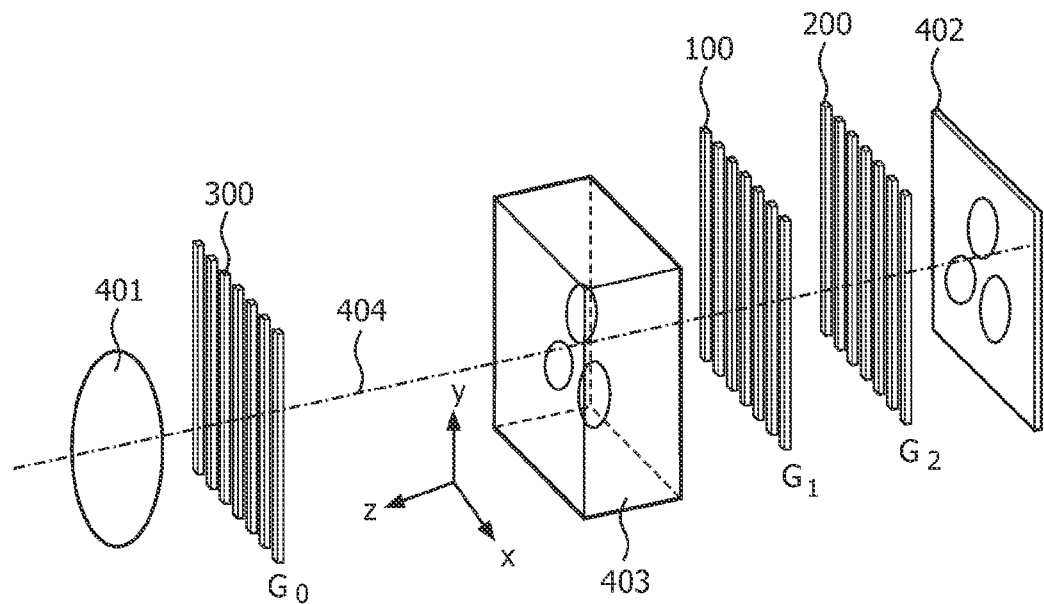
FIG. 1A shows a DPCI used for an imaging apparatus according to the invention.

The illustration in the drawings is schematically and not to scale. In different drawings, similar or identical elements are provided with the same reference numerals.

FIG. 1A shows a measurement setup for differential phase-contrast imaging (DPCI setup). The imaging apparatus comprising a source of electromagnetic radiation, for example an X-ray source or an optical source, symbolized by the focal spot 401. After the source, an absorption or source grating 300 (G0) is arranged for spatial beam coherence. The incoherent X-ray source used is symbolized by the focal spot 401. The radiation beam emitted by the source has an optical axis 404. First, the beam passes the absorption grating 300. Then, the beam passes the object of interest 403 and then the phase grating 100 (G1). After that, the beam passes a second absorption grating 200 (G2), which is arranged before the imaging detector 402.

The phase grating 100 is adapted for producing an interference pattern between G1 and G2.

Figure 1B:
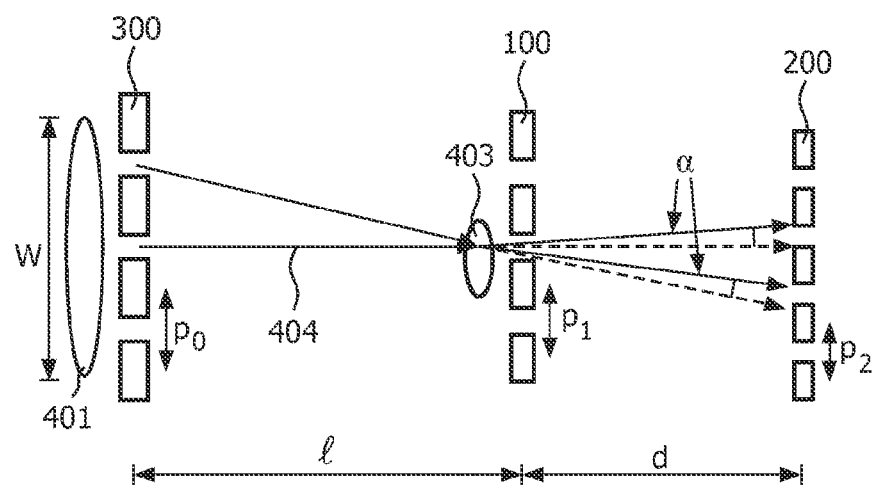
FIG. 1B shows a cross-section of the setup depicted in FIG. 1A.

FIG. 1B shows a cross-section of the imaging setup of FIG. 1A. The grating 300 has a first pitch $p_0$, the phase grating 100 has a second pitch $p_1$ and the second absorption grating 200 has a third pitch $p_2$. The distance between the gratings 300, 100 is 1 and the distance between the gratings 100 and 200 is d which correspond to the Talbot distance.

Figure 1C:
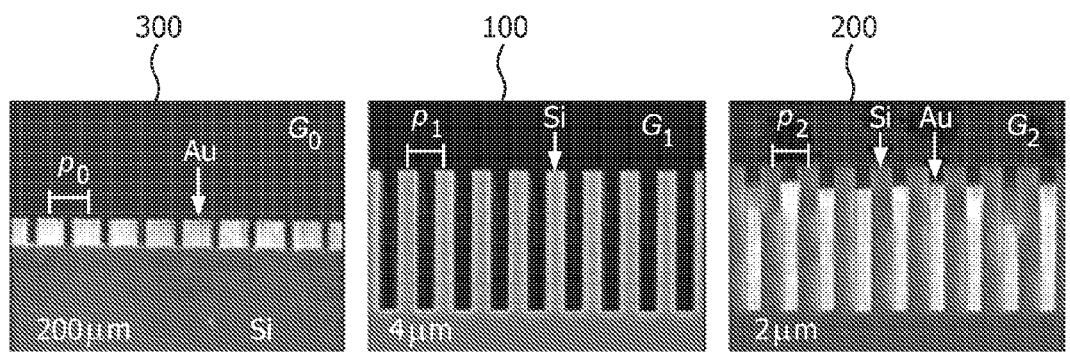
FIG. 1C shows cross-sections of gratings G0, G1 and G2 in rectangular, non-tilted geometry.

FIG. 1C shows cross-sections of the three gratings 300, 100, 200. As can be seen from FIG. 1C, the gratings 300 and 200 are filled with gold. Wherein the phase grating 100 (in the middle) has trenches which are not filled, but etched into the silicon substrate.

Figure 2:
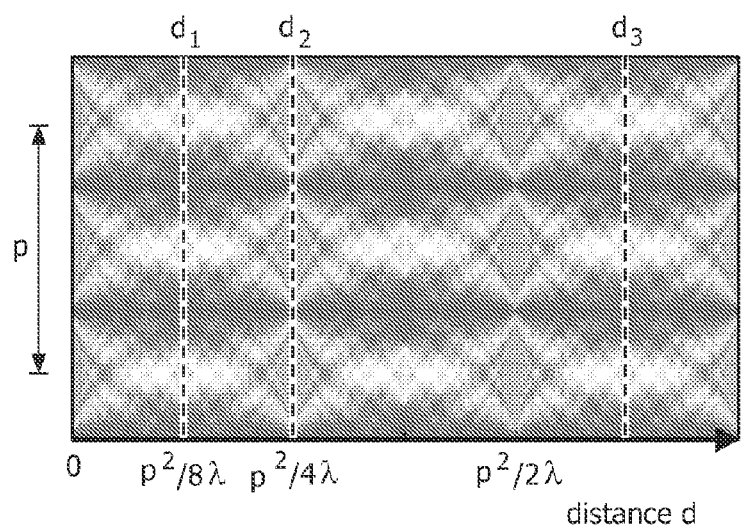
FIG. 2 shows an interference pattern created between G1 and G2.

FIG. 2 shows an interference pattern created between G1 and G2, demonstrating the "self-imaging" effect of the grid in characteristic distances $d_1$, $d_2$ and $d_3$ (Talbot effect). The relative position of the minima and maxima depends on the phase-shift of the wave front incident on G1. In currently used DPCI setups, $d_1$ is typically in the order of several cm.

Figure 3:
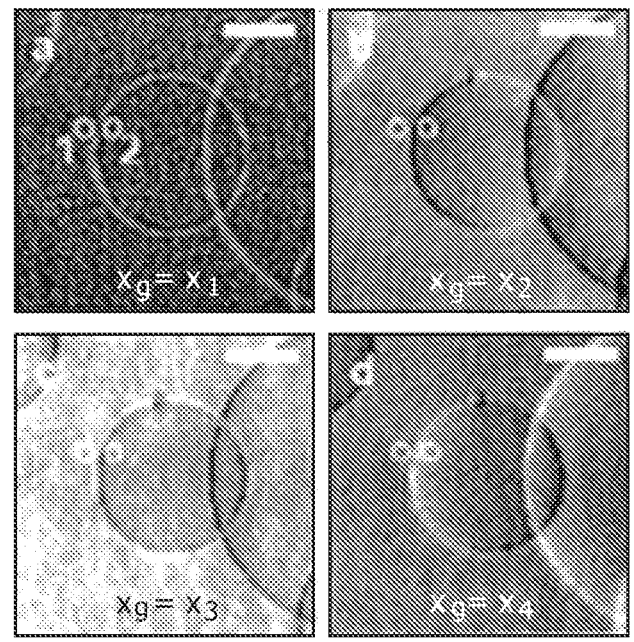
FIG. 3 shows the detection of the "differential phase-contrast" by shifting the absorber grid G2.
Figure 3:
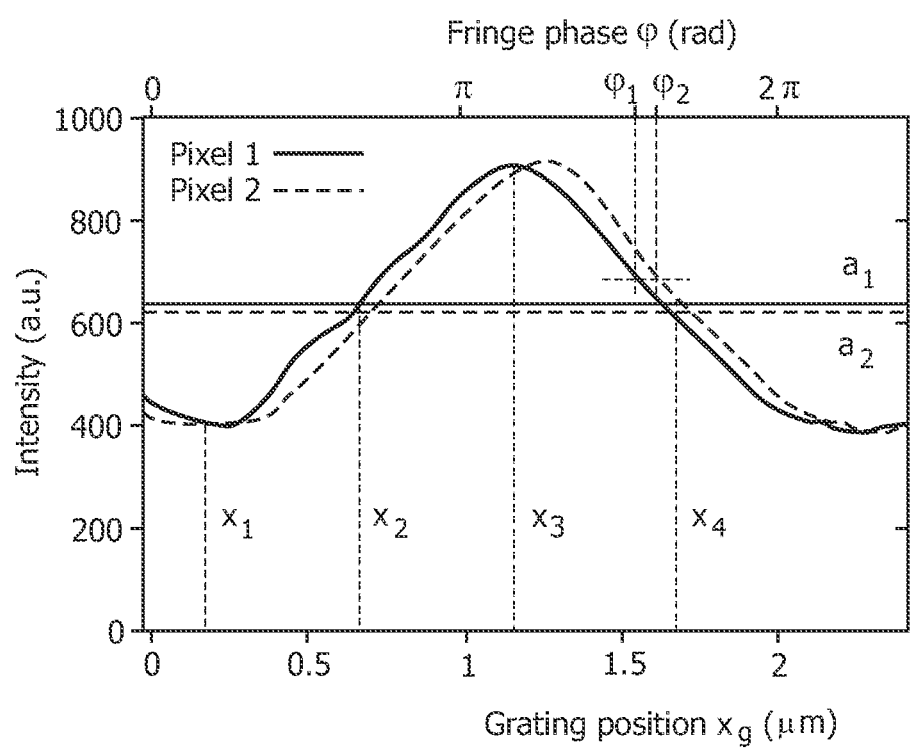

FIG. 3 shows the detection of the "differential phase-contrast" by shifting the absorber grid G2 in a direction x perpendicular to the optical axis and perpendicular to the orientation of the grating lines in a cross-sectional view perpendicular to the optical axis. The difference in the wave front phase at two positions "1" and "2" can be extracted from the phase-shift $\phi_2-\phi_1$ of the measured Moire pattern, here for four sampling positions $x_1$ to $x_4$.

One of the critical topics for the realization of a system for human imaging is the cone-beam geometry that is necessary for the imaging of larger objects like for example in mammography or neuro applications. In the case of non-focused gratings, typically a strong phase-contrast deterioration in regions outside the centre FOV is seen, as a rectangular structure creates a trapezoid profile in a projection with a particular angle to the optical axis. For the adaption to the cone-beam geometry it may be necessary to have focused trench structures for the gratings G0, G1 and G2.

Figure 4:
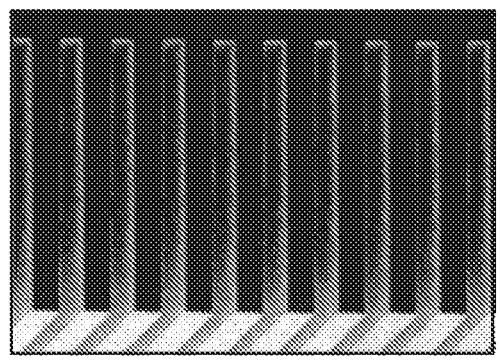
FIG. 4 shows a part of a grating with non-tilted trenches.

Methods of wet etching (e.g. with the help of heated Potassium Hydroxide (KOH) solutions which can be used for crystallographic etching of silicon) or DRIE (Deep Reactive Ion Etching) may be used to etch trenches with a high aspect ratio into a silicon wafer. The regular structure within a defined pitch is a critical parameter. As the requirements for the aspect ratio for the etching—but later also for the filling with an absorber material are quite demanding, the gratings are usually realized with a parallel structure (see FIG. 4).

According to the invention, the structuring of the grating results in a focused grating geometry. As the etching process is an isotropic process it may be necessary to bring trenches in the preferred direction into the silicon.

It is possible to drill holes in silicon and also to structure areas with a laser. However, the surface structure of a laser-drilled hole may be not as perfect as it is needed for the gratings.

Thus, the following two steps are performed:

1. Trenches are "written" into silicon wafer along the grating line direction but with a slight increased angle from trench to trench. This gives the rough "focusing" direction of the overall structure. During the trench "writing" process the laser (or other appropriate source of electromagnetic radiation) has to be focused to the different depth inside the silicon and also the beam shape has to be adapted to achieve an almost straight profile line at the side of the trench.

2. The post-processing step is an etching step to "clean" and smoothen the surfaces and to optimize the grating structure.

The following figures illustrate the geometries of the grating and the measurement setup.

Figure 5:
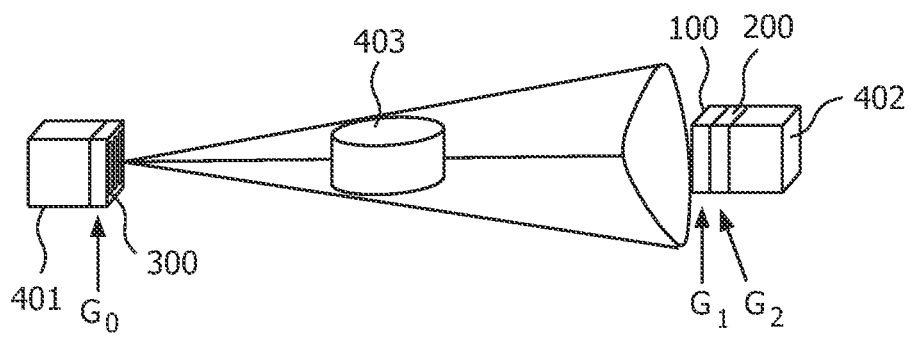
FIG. 5 shows a setup for an imaging apparatus according to an exemplary embodiment of the invention.

FIG. 5 shows a measurement setup for an imaging apparatus according to an exemplary embodiment of the invention.

In direction of the optical axis, the source grating 300 (G0) is arranged behind the X-ray source 401. Next in order, the beam transmits an object of interest 403. Next in order, the beam passes the phase grating 100 (G1) followed by the absorption grating 200 (G2) before being detected.

Figure 6:
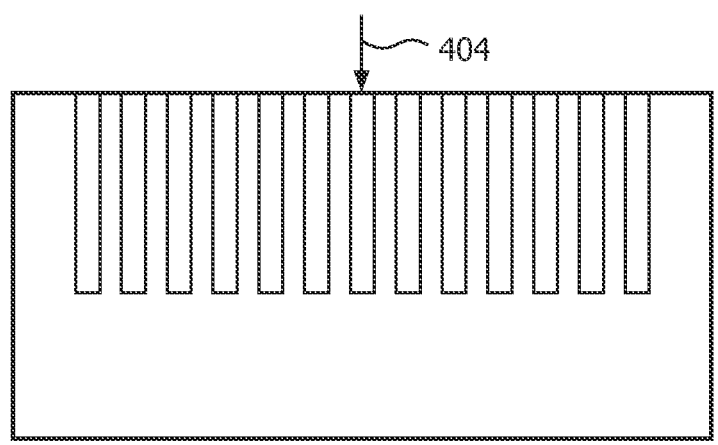
FIG. 6 shows another cross-section of a grating with parallel trenches.

FIG. 6 shows a cross-section of a grating with parallel trenches. The angle between the optical axis 404 (identical to the primary axis) and the trenches is 0 degrees. In other words, the trenches are non-tilted trenches.

Figure 7:
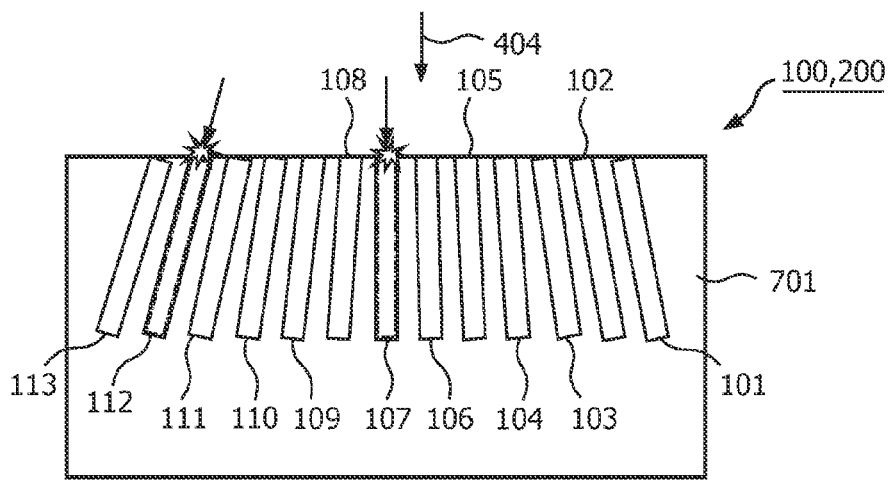
FIG. 7 shows a cross-section of a grating with angular tilted trenches according to an exemplary embodiment of the invention.

FIG. 7 shows a cross-section (not to scale) of angular tilted trenches which have been formed by a laser beam (focusing to the depth and tilting) and are located inside a wafer material 701. Each of the trenches 101 to 113 has a different tilted angle with respect to the optical or primary axis 404.

As can be seen from FIG. 7, the laser beam has an incident angle corresponding to the tilting angle of each trench. However, after laser beam writing the wall of the trenches may be not smooth enough for optimal image quality.

Figure 8:
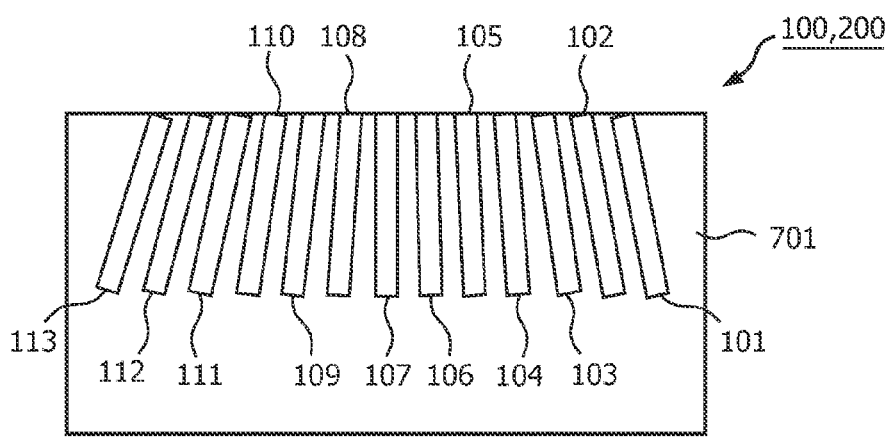
FIG. 8 shows a cross-section of the grating of FIG. 7 after post-processing.

FIG. 8 shows a cross-section of the grating 100, 200 depicted in FIG. 7 after post-processing with an appropriate etching step. The walls of the trenches 101 to 113 are now smooth.

Another extension of the structuring technique results in a focused and trapezoid design of the G0 grating 300. In addition to a focused design, a trapezoid shape for each trench 901-908 allows X-rays or other beams of electromagnetic radiation to pass in a broader angular distribution, i.e. the output of such a G0 grating is increased.

Figure 9:
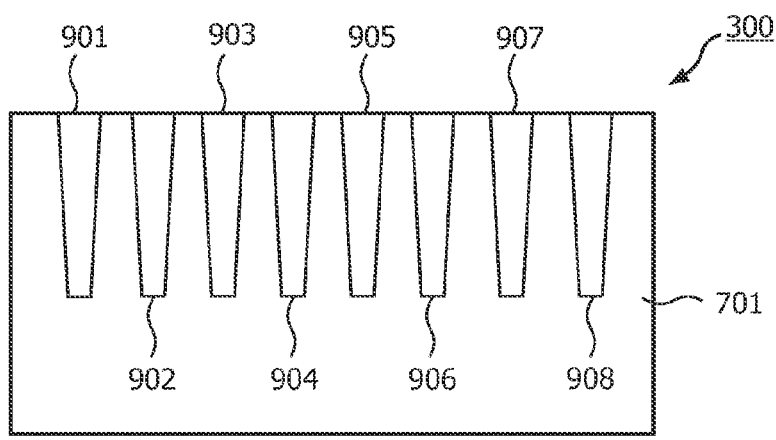
FIG. 9 shows a cross-section of an absorption grating G0 in trapezoid geometry.

This may be performed with Deep Reactive Ion Etching (DRIE etching) technology by reducing the parameter for etching in relation to the isolation step in the "Bosch" process. In such a way a more closing (or opening) trench geometry can be realized. This is depicted in FIG. 9.

An obstacle in the translation of X-ray differential phase-contrast imaging towards higher X-ray energies is the production of phase gratings and absorption gratings with high aspect ratio. If the distance between these two gratings is kept constant, the aspect ratio R of the phase grating increases like $E^{3/2}$, wherein E is the X-ray energy. The limit in aspect ratio R of state-of-the-art fabrication of gratings made from silicon is currently between 15 and 20, depending on many factors like pitch (in the region of a few microns), surface roughness, etc. Therefore, the range of usable energies for DPC currently ends at about 30 to 40 keV.

In other words, the trench depth is proportional to E for constant (pi) phase shift and the depth goes like $1/\sqrt{E}$ due to the Talbot condition.

In the following, a simple and effective way to overcome the above restrictions is disclosed, allowing the application at higher X-ray energies without the need to go to gratings with higher physical aspect ratios (adaptive to energy).

Especially the phase grating could be tilted adaptively to the selected mean energy of the X-ray spectrum.

In the usual concept of DPC, the X-ray photons are incident perpendicular to the grating surface. The central idea of the above and in the following described invention consists of aligning the grating normal at a given angle with respect to the incoming X-rays by rotating the gratings around an axis perpendicular to both, the direction of the incoming X-rays and the direction determined by the lines of the gratings. This can be achieved by rotation of the gratings or, as depicted in FIG. 12c, by tilting the gratings with respect to the substrate surface and thus with respect to the primary axis.

As can be seen from FIG. 10, the effective aspect ratio $R_{eff}$ is related to the physical aspect ratio R via $R_F = R/\cos \alpha$, wherein $\alpha$ 1003 is the angle between the incident rays 1002 and the grating normal 1001 (see FIG. 11). The grating is referenced with numeral 1000.

In other words, the effective aspect ratio $R_F$ in the case of FIG. 11 is higher by a factor of $1/\cos \alpha$ with respect to the case depicted in FIG. 10 where the incident beam is parallel to the surface normal 1001.

Since the phase grating and the absorption grating are part of a Talbot interferometer, both gratings should be tilted with respect to the incoming X-rays while staying parallel with respect to each other. For small angles $\alpha$ it may be feasible to keep also the detector parallel to the gratings (see FIG. 12a).

However, for higher angles, the detectors 402 may be kept perpendicular to the optical or primary axis 404 of the system (direction of X-ray propagation). See for example FIG. 12B. In this case it may be necessary to correct for the different lengths of the propagation before and after phase/absorption grating pair 100, 200.

As can be seen from FIG. 12C, both gratings 100, 200 and the detector 402 are arranged perpendicular to the incoming X-rays 404. However, the gratings 100, 200 have trenches 101, 102, 103, 104 etc., which are tilted with respect to the optical axis 404 such that the walls of the trenches are not in the same plane as the optical axis 104. Reference numerals 1202, 1203 show two walls of the trenches, which may be grown on the substrate 1201. Alternatively, the trenches may be etched in the above described etching process The embodiment of FIG. 12C reduces the distance between phase and absorption grating 100, 200 and allows that the detector 402 can be positioned right after the absorption grating 200 (G2).

FIG. 13 shows a flow-chart of an exemplary embodiment of the invention. In step 1301 the trenches are pre-fabricated or "written" by a controlled laser beam or other radiation beam. In step 1302 the trenches are post-processed by etching in order to smooth the surfaces.

The present invention applies to imaging systems that are based on the gratings interferometer type as disclosed in Pfeiffer et al., Nature Physics 2, 258 (2006).

In particular, an application of the invention can be found in all modalities related to differential phase-contrast imaging, i.e. in stationary transmission geometries (i.e. mammography, fluoroscopy, etc.), but also computed tomography and related rotational X-ray imaging technologies.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

LIST OF REFERENCE SIGNS

100 Phase grating G1
200 Absorption grating G2
300 Absorption grating G0
101-113 Tilted trenches
401 Source or focal spot of radiation beam
402 Detector
403 Object of interest
404 Optical axis
901-908 Trapezoid trenches
1000 Grating
1001 Surface normal
1002 Incident beam
1003 Angle α
1201 Substrate
1202, 1203 Trenches
1301, 1302 Method steps

The invention claimed is:

1. A method for fabricating a grating for a phase contrast imaging apparatus for examining an object of interest, the grating having a primary axis which is arranged in a direction towards a source of radiation when the grating is installed in the imaging apparatus, the method comprising the steps of: writing, with a beam of electromagnetic radiation, at least a first trench into a wafer material; smoothing surfaces of the written first trench by etching technology; wherein the first trench has a depth in a first direction; wherein the first direction is different from the primary axis, such that the first trench is tilted by a first angle with respect to the primary axis.

2. The method of claim 1, further comprising the step of: filling at least a first trench with an absorbing material.

3. A grating for a phase contrast imaging apparatus for examining an object of interest, the grating having a primary axis which is arranged in a direction towards a source of radiation when the grating is installed in the imaging apparatus, the grating comprising:
a wafer material having inside:
a first trench having a depth in a first direction, the first direction being different from the primary axis, such that the first trench is tilted with respect to the primary axis, said grating comprising a substrate that has a surface perpendicular to said primary axis, the first trench being tilted by a first angle with respect to the primary axis; and
a second trench tilted by a second angle with respect to the primary axis, the first angle being smaller than the second angle,
said source serving as a focal spot of said radiation.

4. The grating of claim 3, fabricated by a method comprising the steps of: writing, with a beam of electromagnetic radiation, said first trench into said wafer material; smoothing surfaces of the written first trench by etching technology; wherein said first trench has a depth in said first direction; wherein said first direction is different from said primary axis, such that said first trench is tilted by said first angle with respect to said primary axis.

5. The grating of claim 3, said wafer material having inside: a sequence of trenches that includes the first and second trenches, wherein each trench of the sequence of trenches is tilted by a respective angle with respect to the primary axis, and wherein the respective angle increases from trench to trench.

6. The grating of claim 5, wherein the grating allows for an operation of the imaging apparatus in a focused geometry.

7. The grating of claim 6, wherein the trenches are at least one of linear trenches, trapezoid trenches, and asymmetric trenches in focused geometry.

8. A phase contrast imaging apparatus for examining an object of interest, the apparatus comprising:
a source for emitting a beam of radiation;
a detector;
a grating positioned between the source and the detector;
wherein the detector is configured for detecting the radiation after it has passed the object of interest and the grating);
wherein the grating has a focused geometry;
wherein the grating has a primary axis which is arranged in a direction towards a source of radiation when the grating is installed in the imaging apparatus, the grating comprising:
a wafer material having inside:
a first trench having a depth in a first direction, the first direction being different from the primary axis, such that the first trench is tilted with respect to the primary axis, said grating comprising a substrate that has a surface perpendicular to said primary axis, the first trench being tilted by a first angle with respect to the primary axis; and
a second trench tilted by a second angle with respect to the primary axis, the first angle being smaller than the second angle,
said source serving as a focal spot of said radiation.

9. The imaging apparatus of claim 8, said wafer material having inside: a sequence of trenches that includes the first and second trenches, wherein each trench of the sequence of trenches is tilted by a respective angle with respect to the primary axis, and wherein the respective angle increases from trench to trench.

10. The imaging apparatus of claim 9, further comprising: a second grating which is an absorption grating positioned in front of the detector; wherein the second grating has also a focused geometry configured to the grating position.

11. The imaging apparatus of claim 10, further comprising: a third grating which is an absorption grating having a trapezoid geometry and positioned between the source and the phase grating and which allows for an at least partially coherent illumination of the phase grating.

12. The imaging apparatus of claim 11, further comprising: at least one actuator or stepper motor; wherein the beam of radiation emitted by the source has an optical axis; wherein the actuator or stepper motor is configured for at least one of moving at least one of the phase grating and the second grating perpendicular to the optical axis of the beam of radiation emitted by the source and changing an effective trench depth for the incident beam of radiation by tilting the grating to a certain angle.

13. The imaging apparatus of claim 11, wherein the source is an x-ray source; and wherein the apparatus is configured as an x-ray based differential phase contrast imaging apparatus.

14. The grating of claim 3, said radiation comprising radiation for phase contrast imaging by said apparatus.

15. The grating of claim 14, said first trench having an inside surface disposed so as to face in a direction opposite to a direction of arrival of said radiation for phase contrast imaging.

16. The grating of claim 8, said radiation comprising radiation for phase contrast imaging by said apparatus.

17. The grating of claim 16, said first trench having an inside surface disposed so as to face in a direction opposite to a direction of arrival of said radiation for phase contrast imaging.

18. The method of claim 1, said grating comprising a substrate that has a surface perpendicular to said primary axis, said wafer material having inside a second trench tilted by a second angle with respect to the primary axis, the first angle being smaller than the second angle.

19. The grating of claim 3, the first and second trenches facing in respective directions that tilt toward said primary axis.

20. The grating of claim 19, said grating having a focused geometry with respect to said spot.

21. The grating of claim 8, the first and second trenches facing in respective directions that tilt toward said primary axis.

22. The grating of claim 21, said focused geometry comprising a focused geometry with respect to said spot.

* * * * *